United States Patent
Danziger

(10) Patent No.: US 9,462,766 B2
(45) Date of Patent: Oct. 11, 2016

(54) *EUPHORBIA* 'DEUPHBLISS'

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 16 days.

(21) Appl. No.: 14/595,933

(22) Filed: Jan. 13, 2015

(65) Prior Publication Data

US 2016/0198669 A1    Jul. 14, 2016

(51) Int. Cl.
*A01H 5/02*  (2006.01)
*A01H 5/10*  (2006.01)
*A01H 1/02*  (2006.01)

(52) U.S. Cl.
CPC . *A01H 5/10* (2013.01); *A01H 1/02* (2013.01)

(58) Field of Classification Search
USPC .......................................................... Plt./302
See application file for complete search history.

(56) References Cited

PUBLICATIONS

Mueller 2011, Aggie Horticulture, HortUpdate, Nov./Dec. 2011 edition.*

* cited by examiner

*Primary Examiner* — David H Kruse
(74) *Attorney, Agent, or Firm* — Cassandra Bright

(57) ABSTRACT

A new and distinct *Euphorbia* cyathophora plant named 'DEUPHBLISS' characterized by tall plant height with large, ornamental floral bracts. Floral bracts are distinctively colored near Green N137A, Red 42A and Black 203A. Plant height commonly averages 1 meter. Plants have commercial use for cut flowers or ornamental plants.

Figure 1:

6 Claims, 2 Drawing Sheets
(2 of 2 Drawing Sheet(s) Filed in Color)

*EUPHORBIA* 'DEUPHBLISS'

FIELD OF THE INVENTION

The present invention relates to a new, distinct and stable variety of *Euphorbia* cyathophora, hereinafter referred to as 'DEUPHBLISS'. The present invention relates to seeds which are the *Euphorbia* cyathophora 'DEUPHBLISS', as well as, plants and plant parts produced by these seeds which have all of the morphological and physiological characteristics of the *Euphorbia* cyathophora 'DEUPHBLISS'. The present invention also relates to methods for producing these seeds and plants of the *Euphorbia* cyathophora 'DEUPHBLISS'. Furthermore, the present invention relates to a method of producing progeny *Euphorbia* plants by crossing *Euphorbia* 'DEUPHBLISS', as either the female or seed or male or pollen parent, with another *Euphorbia* plant and selecting progeny.

BACKGROUND OF THE INVENTION

The present invention relates to a new, distinct and stable variety of *Euphorbia* cyathophora, and hereinafter referred to by the variety denomination 'DEUPHBLISS'. The new *Euphorbia* 'DEUPHBLISS' originated from a self-crossing made in a controlled breeding program by the inventor in June 2012, and then first flowered and selected in June 2013, in Mishmar Hashiva, Israel. The parent is the *Euphorbia* cyathophora proprietary line identified by code EP-101 (unpatented). This proprietary line is the sole parent, as the resulting 'DEUPHBLISS' is the result of a self-crossing of this single parent variety.

*Euphorbia* cyathophora is a member of the Euphorbiaceae family. *Euphorbia* cyathophora is a vascular land plant, native to Mexico, and now naturalized in most regions of the United States. For the most part, plants of *Euphorbia rurale* are herbaceous annuals.

To the inventor's best knowledge, there have not been significant commercial efforts to date to hybridize and produce new and interesting *Euphorbia* cyathophora varieties, although many of species of *Euphorbia* have been developed extensively for ornamental purposes.

Over time, the inventor has trialed *Euphorbia* cyathophora and found it may be advantageously grown for ornamental horticultural uses. The inventor found this Genus and species could be employed for commercial cut flower purposes.

Bracts of *Euphorbia* can be highly ornamental, while true flowers are often insignificant. Many types of *Euphorbia*, including the commercially known Poinsettia, are grown for the ornamental value of the floral bracts.

Asexual propagation of *Euphorbia* can be performed by vegetative terminal cuttings, however, this is not common practice; propagation is most commonly performed by sowing seeds.

Methods for cultivation of *Euphorbia* are moderately well known. Reference to the species can be found in *Euphorbia* Planetary Biodiversity Inventory (version 2011). Additionally short reference can found in; *Euphorbias*: A Gardeners' Guide. Timber Press, Portland, Oreg. 192 p.), which is herein incorporated by reference.

The *Euphorbia* cyathophora seeds and plants produced by this method are uniform with respect their morphological and physiological characteristics.

A need exists for a greater variety of *Euphorbia* cultivars with practical and attractive ornamental features. Additionally, a need exists for additional *Euphorbia* cyathophora cultivars that can be easily propagated by seed, with consistent results. The new *Euphorbia* 'DEUPHBLISS' was developed through a controlled breeding program and exhibits unique, desirable and stable characteristics.

SUMMARY OF THE INVENTION

The present invention provides *Euphorbia* plant selections that produce large, colorful ornamental floral bracts on tall plants. Plants of this new variety have shown consistency in producing commercial quantities of large, showy floral bracts on long stems. This interesting feature is both novel and useful, as it can be successfully used in flower bouquets both as featured, or filler stem material. These qualities distinguish the new cultivar from typical *Euphorbia* cyathophora varieties.

These and other objectives have been achieved in accordance with the present invention which provides 'DEUPHBLISS' as a new *Euphorbia* cultivar that is a product of a planned breeding program conducted by the inventor, Gavriel Danziger, in Moshav Mishmar Hashiva, Israel in 2012. The parent is the *Euphorbia* cyathophora inbred line identified by code EP-101 (unpatented).

The parental cultivar has a sufficient degree of homozygosity such that the progeny of the cross are genetypically and phenotypically uniform. The new *Euphorbia* cyathophora 'DEUPHBLISS' therefore can be produced by sexual reproduction by self crossing the parent inbred line identified by the code EP-101 to produce a population of progeny plants, each of which has the combination of characteristics as herein disclosed for the new *Euphorbia* cyathophora 'DEUPHBLISS'.

Seeds which are variety 'DEUPHBLISS' are produced by crossing the parental inbred line identified by the code EP-101 and are deposited with the Korean Collection for Type Cultures (KCTC), Biological Resource Center, Korea Research Institute of Bioscience and Biotechnology (KRIBB), 125 Gwahak-ro, Yuseong-gu, Daejeon 305-806, Korea having deposit Designation. KCTC-12899BP.

OBJECTS OF THE INVENTION

The present invention relates to seeds which produce *Euphorbia* cyathophora 'DEUPHBLISS'. The present invention also relates to *Euphorbia* plants, and parts thereof; having all the physiological and morphological characteristics of *Euphorbia* cyathophora 'DEUPHBLISS'. The present invention relates to a plant produced from seeds which are *Euphorbia* cyathophora 'DEUPHBLISS'. The present invention also relates to plant parts, such as pollen, seeds or inflorescence produced by *Euphorbia* cyathophora 'DEUPHBLISS'.

The present invention relates to a method of producing seed which are *Euphorbia* cyathophora 'DEUPHBLISS', by performing a self-crossing of *Euphorbia* cyathophora inbred line identified by code EP-101 (unpatented) and harvesting seeds produced from said cross.

The present invention also relates to a method of producing plants having all the physiological and morphological characteristics of the *Euphorbia* cyathophora 'DEUPHBLISS' comprising the steps of (a) self-crossing *Euphorbia* cyathophora inbred line identified by code EP-101 (unpatented) (b) harvesting seeds produced from said cross; and (c) producing plants from said harvested seeds.

The present invention also relates to producing progeny plants from the cross of *Euphorbia* cyathophora 'DEUPH- BLISS', as the female or male parent, with another *Euphorbia* plant, and selecting progeny plants from this cross.

BRIEF DESCRIPTION OF THE PHOTOGRAPHS

The patent or application file contains at least one drawing executed in color. Copies of this patent or patent application publication with color drawings will be provided by the Office upon request and payment of the necessary fees.

The accompanying photographs illustrate the overall appearance of the new *Euphorbia* cyathophora 'DEUPHBLISS' showing the colors as true as is reasonably possible with colored reproductions of this type. Colors in the photographs may differ slightly from the color values cited in the detailed botanical description which accurately describes the color of 'DEUPHBLISS'.

Figure 2:

FIG. 1 shows a side view perspective of a typical flowering stem of 'DEUPHBLISS', at approximately 6 months of age FIG. 2 shows multiple flowering stems, with typical floral parts and foliage.

DETAILED BOTANICAL DESCRIPTION

The present invention was created by the inventor, Gavriel Danziger during 2011, and flowered for the first time in 2013 in Mishmar Hashiva, Israel.

This invention is directed to *Euphorbia* plant having all the morphological and physiological characteristics of the variety 'DEUPHBLISS' produced from seeds which are the product of the self-cross of the *Euphorbia* cyathophora inbred line identified by code EP-101 (unpatented). The parent has a sufficient degree of homozygosity such that the progeny of the cross were, and continue to be, phenotypically uniform. The new variety 'DEUPHBLISS' can therefore be produced by sexual reproduction by crossing of the inbred selection identified by the code EP-101 to produce a population of progeny plants, each of which has the combination of characteristics herein disclosed for the new variety 'DEUPHBLISS'.

The following traits have been repeatedly observed and are determined to be unique characteristics of 'DEUPHBLISS' which in combination distinguish this *Euphorbia* as a new and distinct cultivar:
1. Typically 12 red colored floral bracts
2. Unique black margin of floral bracts
3. Tall growth; plants reaching 1 meter in height.
4. Suitability for production and use as a cut flower The inventor is unaware of other commercial cultivars of *Euphorbia* cyathophora similar to the new variety 'DEUPHBLISS'. Search by the inventor has not resulted in discovery of known *Euphorbia* cyathophora cultivars used for ornamental cut flower purposes.

'DEUPHBLISS' has not been tested and observed under all possible environmental conditions. The phenotype of the new cultivar may vary with variations in environment such as temperature, light intensity, frequency of fertilization, composition of fertilizer, acetylene treatment, day length and humidity, without any change in the genotype of the plant.

For example, substantial differences in plant height and diameter, number of leaves, and branches can result depending on the growing conditions. Typically these plants are produced outdoors, and variations in temperature, light conditions and humidity can produce different results.

The aforementioned photographs, together with the following observations, measurements and values describe the new *Euphorbia* 'DEUPHBLISS' as grown outdoors in Moshav Mishmar Hashiva, Israel, under conditions which closely approximate those generally used in commercial practice. Plants of 'DEUPHBLISS' were grown outdoors with day temperatures ranging from 28° C. to 30° C. and night temperatures ranging from 19° C. to 20° C. No artificial lighting or photoperiodic treatments were conducted. This open field planting was not shaded.

Color references are made to the Royal Horticultural Society Colour Chart (RHS), 2005 mini edition, except where general colors of ordinary significance are used. Color values were taken under daylight conditions in a greenhouse Mishmar Hashiva, Israel. The age of the plants of 'DEUPHBLISS' described is about 150 days from planting a seedling plant. The seedling plant is approximately 5 weeks old.

BOTANICAL CLASSIFICATION: *Euphorbia cyathophora*
    Parentage:
        Parent: *Euphorbia cyathophora* inbred line identified by code EP-101 (unpatented)
    Plant:
Growth Habit: upright
Height: Approximately 1 meter
Plant Spread: Approximately 60 cm.
Growth Rate: Approximately 5 months to achieve 100 cm.
Length of Primary Lateral Branches: 75 cm.
Diameter of Lateral Branches: 0.5 cm.
Quantity of Primary Lateral Branches: Average 10 per plant
Texture of Lateral Branches: Glabrous
Lateral Branch Shape: Rounded with ridges.
Lateral Branch Strength: strong, flexible.
Lateral Branch Color: Near RHS Yellow-Green 147B
Internode Length: 6 cm.
Number of Leaves per Lateral Branch: Average 23.
Age of Plant Described: Approximately 150 days.
    Foliage:
        Arrangement: Alternate, single.
        Shape of blade: Elliptic.
        Average Length: Approximately 7 cm.
        Average Width: Approximately 3.5 cm.
        Apex: Apiculate.
        Base: Cuneate.
        Attachment: Stalked
        Margin: Entire
        Texture of top surface: Glabrous.
        Texture of bottom surface: Scabrous.
        Leaf internode length: Approximately 1 cm, 0.5 cm near inflorescence.
        Color:
        Young foliage upper side: Near R.H.S. Green N137
        Young foliage under side: Near R.H.S Green 137D.
        Mature foliage upper side: Near R.H.S. Green 137C
        Mature foliage under side: Near R.H.S. Yellow-Green 147C
        Venation:
        Type: Anastomosing.
        Venation color upper side: Near R.H.S. Yellow-Green 147B
        Venation color under side: Near R.H.S. Yellow-Green 147A
        Durability of foliage to stresses: Good.
Petiole:
    Average Length: Approximately 15 mm.
    Diameter: Approximately 2 mm.

Color: Near R.H.S. Yellow-Green 146C
Strength: Strong, flexible.
Inflorescence:
Bloom Period:
  Natural Season: May-November. (Israel)
  Greenhouse Production: Approximately 6 weeks to flowering
Inflorescence:
  Arrangement: Terminal cluster.
  Type: Cyathium, irregular.
  Height: Approximately 1.5 cm.
  Width: Approximately 8 cm.
Bud:
  Bud shape: Ovoid.
  Bud length: Approximately 5 mm.
  Bud diameter: Approximately 3 mm.
  Bud color: Near RHS Yellow-Green 146C.
Floral Bracts:
Arrangement: Imbricate.
Shape: Oblanccolate.
Apex: Acute.
Base: Cuneate
Length: 3.0 cm.
Width: 1.0 cm.
Texture: Glabrous
Color:
  Upper side of immature bract: Near RHS Green N137
  Under side of immature bract: Near RHS Green 137D
  Upper side of mature bract: Base and interior near RHS Red 42C With black rim around Red coloration, near RHS 203B. Green near RHS N137A from black rim through bract margin.
  Under side of mature bract: Near RHS 137C
Peduncle:
  Length: Approximately 0.5 cm.
  Diameter: Approximately 2 mm.
  Angle: Approximately 45 degrees from center of whorl
  Strength: Strong.
  Color: Near RHS Yellow-Green 147C.
Pedicel:
  Length: Approximately 2 mm.
  Diameter: Approximately 1 mm.
  Angle: Approximately 45 degrees.
  Strength: Flexible
  Color: Near RHS Yellow-Green 147C
Fragrance: Not fragrant
  Reproductive Organs:
Number of pistils per flower: 1
  Pistil Length: Approximately 1 mm.
  Stigma shape: Crown like.
  Stigma color: Near RHS Yellow 5C.
  Style color: Near RHS Yellow 5C
  Style length: Approximately 0.5 mm.
  Ovary Color: Near RHS Yellow-Green 147B.
  Stamens Quantity: 6
  Stamen Length: 0.5 mm
  Anther shape: Oblate
  Anther Size: 0.1 mm
  Anther color: Near RHS Green-Yellow 1B
  Pollen color: Near RHS Yellow 5A
  Pollen Quantity: Moderate
  Temperature tolerance: Tolerates a range from approximately −5° C. to 40° C.
  Seeds/Fruit:
Fruits
Shape: 3 compartment capsule
Length: Approximately 5 mm.
Width: Approximately 4 mm
Color: Near RHS Green N137A
Texture: Smooth
Seeds
Shape: oblong
Color: Near RHS Black 203A
Length: 1 mm
Width: 0.5 mm.
DISEASE/PEST RESISTANCE AND SUSCEPTIBILITY: Neither resistance nor susceptibility to normal diseases and pests of *Euphorbia* observed.

We claim:
1. A *Euphorbia* plant named 'DEUPHBLISS', representative seed deposited at the Korean Collection for Type Cultures (KCTC) having deposit Designation KCTC-12666BP.
2. A *Euphorbia* seed hat produces the plant of claim 1.
3. A plant part obtained from the *Euphorbia* plant of claim 1.
4. A method of producing *Euphorbia* progeny plant comprising the steps of
  (a) crossing *Euphorbia* DEUPHBLISS', produced from representative seed deposited with the Korean Collection for Type Cultures (KCTC,) having deposit Designation KCTC-12899BP as a female or male parent with a second *Euphorbia* plant, and (b) selecting progeny.
5. The method according to claim 4, wherein the second *Euphorbia* plant is 'DEUPHBLISS.
6. A hybrid progeny plant produced by the method of claim 4 wherein the second *Euphorbia* plant is other than 'DEUPHBLISS'.

* * * * *